(12) United States Patent
Ghosh et al.

(10) Patent No.: US 10,865,167 B2
(45) Date of Patent: Dec. 15, 2020

(54) HYDROCRACKING PROCESS

(71) Applicant: SABIC GLOBAL TECHNOLOGIES B.V., Bergen op Zoom (NL)

(72) Inventors: Ashim Kumar Ghosh, Sugar Land, TX (US); Alla Khanmamedova, Sugar Land, TX (US); Scott A. Stevenson, Sugar Land, TX (US); Luis Aramburo, Geleen (NL); David L. Sullivan, Little Ferry, NJ (US); Cong Nguyen, Sugar Land, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 9 days.

(21) Appl. No.: 16/331,828

(22) PCT Filed: Sep. 7, 2017

(86) PCT No.: PCT/IB2017/055397
§ 371 (c)(1),
(2) Date: Mar. 8, 2019

(87) PCT Pub. No.: WO2018/047093
PCT Pub. Date: Mar. 15, 2018

(65) Prior Publication Data
US 2019/0375696 A1 Dec. 12, 2019

(30) Foreign Application Priority Data
Sep. 12, 2016 (EP) ..................... 16188306

(51) Int. Cl.
| | | |
|---|---|---|
| *C07C 4/06* | (2006.01) | |
| *B01J 23/42* | (2006.01) | |
| *B01J 29/22* | (2006.01) | |
| *B01J 29/44* | (2006.01) | |
| *B01J 35/00* | (2006.01) | |
| *B01J 35/10* | (2006.01) | |

(52) U.S. Cl.
CPC ................ *C07C 4/06* (2013.01); *B01J 23/42* (2013.01); *B01J 29/22* (2013.01); *B01J 29/44* (2013.01); *B01J 35/0066* (2013.01); *B01J 35/1057* (2013.01); *B01J 35/1061* (2013.01); *B01J 2229/186* (2013.01); *C07C 2521/12* (2013.01); *C07C 2523/10* (2013.01); *C07C 2523/42* (2013.01); *C07C 2523/44* (2013.01); *C07C 2529/18* (2013.01); *C07C 2529/40* (2013.01); *C07C 2529/44* (2013.01)

(58) Field of Classification Search
CPC .... C10G 2400/30; C10G 47/18; C10G 45/62; C10G 35/095; C10G 45/70; C10G 2300/104; C10G 2300/1044; C10G 2300/301; C10G 2400/28; B01J 23/42; B01J 29/22; B01J 29/44; B01J 35/0066; B01J 35/1057; B01J 35/1061; B01J 2229/186; B01J 29/74; C07C 4/06; C07C 2521/12; C07C 2523/10; C07C 2523/42; C07C 2523/44; C07C 2529/18; C07C 2529/40; C07C 2529/44

See application file for complete search history.

(56) References Cited

U.S. PATENT DOCUMENTS

| | | | |
|---|---|---|---|
| 3,957,621 A | 5/1976 | Bonacci et al. | |
| 5,191,131 A * | 3/1993 | Takahata | .......... C07C 4/06 585/324 |
| 2002/0082460 A1 | 6/2002 | Verduijn et al. | |
| 2006/0287564 A1 | 12/2006 | Choi et al. | |
| 2009/0272672 A1 | 11/2009 | Arca et al. | |
| 2014/0039233 A1* | 2/2014 | Laha | ............ B01J 35/023 585/417 |
| 2014/0114106 A1 | 4/2014 | Chen et al. | |
| 2017/0121239 A1* | 5/2017 | Fickel | ............ B01J 29/44 |

FOREIGN PATENT DOCUMENTS

| | | |
|---|---|---|
| CN | 105413741 A | 3/2016 |
| WO | 9400409 A1 | 1/1994 |
| WO | 0244306 A1 | 6/2002 |
| WO | 2007055488 A1 | 5/2007 |

(Continued)

OTHER PUBLICATIONS

"Molecular Sieves"; Kirk-Othmer Encyclopedia of Chemical Technology, vol. 16, pp. 811-853.
International Search Report; International Application No. PCT/IB2017/055397; International Filing Date: Sep. 7, 2017; dated Jan. 2, 2018; 6 pages.
Written Opinion; International Application No. PCT/IB2017/055397; International Filing Date: Sep. 7, 2017; dated Jan. 2, 2018; 7 pages.

(Continued)

*Primary Examiner* — Ali Z Fadhel
(74) *Attorney, Agent, or Firm* — Cantor Colburn LLP

(57) ABSTRACT

A process for hydrocracking 2,4-dimethylpentane and/or 2,2,3-trimethylbutane can comprise: contacting a hydrocracking feed stream in the presence of hydrogen with a hydrocracking catalyst, wherein the hydrocracking feed stream comprises at least 0.5 wt % of 2,4-dimethylpentane and/or 2,2,3-trimethylbutane, based upon a total weight of the hydrocracking feed stream; and wherein the hydrocracking catalyst comprises a medium pore zeolite having a pore size of 5-6 Å and a silica to alumina molar ratio of 20-75; preferably the hydrocracking catalyst comprises a medium pore zeolite having a pore size of 5-6 Å and a silica to alumina molar ratio of 20-75 and a large pore zeolite having a pore size of 6-8 Å and a silica to alumina molar ratio of 10-80, wherein the hydrogenation metal is deposited on the medium pore zeolite and the large pore zeolite.

20 Claims, No Drawings

(56) References Cited

FOREIGN PATENT DOCUMENTS

| WO | 2010102712 A2 | 9/2010 |
| WO | 2013182534 A1 | 12/2013 |
| WO | 2015189058 A1 | 12/2015 |

OTHER PUBLICATIONS

China Office Action and Search Report for China Application No. 201780055434.3; Application Filing Date Mar. 8, 2019; dated Jun. 30, 2020; with English Translation, 20 pages.

* cited by examiner

HYDROCRACKING PROCESS

CROSS REFERENCE TO RELATED APPLICATIONS

This application is a 371 of International Application No. PCT/IB2017/055397, filed Sep. 7, 2017, which is incorporated herein by reference in its entirety, and which claims priority to European Application No. 16188306.1, filed Sep. 12, 2016.

The present invention relates to a hydrocracking process.

It has been previously described in WO 02/44306 A1 and WO 2007/055488 A1 that aromatic hydrocarbon compounds and liquefied petroleum gas (LPG) can be produced from a mixed hydrocarbon feedstock having boiling points of 30-250° C. Therefore a hydrocarbon feedstock having boiling points of 30-250° C. and hydrogen is introduced to a reaction zone wherein said hydrocarbon feedstock is converted in the presence of a catalyst to aromatic hydrocarbon compounds abundant in BTX (benzene, toluene, xylene) through hydrodealkylation and/or transalkylation and to non-aromatic hydrocarbon compounds which are abundant in LPG through hydrocracking and recovering the aromatic hydrocarbon compounds and LPG, respectively, through gas-liquid separation and distillation. The methods of WO 02/44306 A1 and WO 2007/055488 produce a product stream comprising a relatively high amount of non-aromatic hydrocarbons that co-boil with BTX rendering it impossible to produce chemical grade BTX without using solvent extraction methods and a relatively high amount of fuel gas at the expense of the LPG produced.

US2009/0272672 discloses a process for the catalytic hydrodealkylation of $C_8$-$C_{13}$ alkyl aromatic compounds mixed with $C_4$-$C_{10}$ aliphatic and cycloaliphatic products which undergo aromatization and subsequent hydrodealkylation. In this process, the hydrocarbons are treated with a ZSM-5 zeolite having the silica to alumina ($SiO_2/Al_2O_3$) molar ratio of 5-100 modified by means of a platinum-molybdenum couple at a temperature of 400 to 650° C., a pressure of 2 to 4 megaPascals (MPa) and hydrogen to feedstock ($H_2$/feedstock) molar ratio ranging from 3 to 6.

US2006/0287564 describes a process for increasing the production of benzene from a hydrocarbon mixture including separating a hydrocarbon feedstock into a $C_6$ or lower hydrocarbon stream and a $C_7$ or higher hydrocarbon stream. The $C_6$ or lower hydrocarbon stream is separated into a non-aromatic hydrocarbon stream and an aromatic hydrocarbon stream through a solvent extraction process. The $C_7$ or higher hydrocarbon stream is subjected to a reaction in the presence of a catalyst comprising platinum/tin or platinum/lead.

U.S. Pat. No. 3,957,621 describes a process for processing heavy reformates from which benzene and lighter components have been largely removed. The removed stream includes the major portion of the benzene in the charge and can include a substantial portion of the toluene.

WO2013/182534 discloses a process for producing BTX from a $C_5$-$C_{12}$ hydrocarbon mixture using a hydrocracking/hydrodesulphurisation catalyst. According to WO2013/182534, the process results in a mixture comprising substantially no co-boilers of BTX, thus chemical grade BTX can easily be obtained. WO2015/189058 discloses a further improvement by selectively recycling back the toluene from the product stream to be included in the feed.

Often, feed streams are purified before being hydrocracked. For example, the feed stream may have been desulfurized, depentanised, and/or processed via extractive distillation. Additionally, different feed streams comprise different concentrations of impurities and if the impurity concentration is low, the existence or issues with that material are not considered or addressed. Therefore, the various patents discussing hydrocracking do not address issues in streams that had higher concentrations of some materials. For example, while WO2013/182534 and WO2015/189058 advantageously provide a chemical grade BTX from many types of feed streams, they do not mention an amount of difficult co-boilers (such as 2,4-dimethylpentane and 2,2,3-trimethylbutane) in the feed stream. The present inventors found that there are some benzene co-boiler compounds which are more difficult to hydrocrack. As a result, there are certain benzene co-boilers (such as 2,4-dimethylpentane and 2,2,3-trimethylbutane) that are avoided in the feed stream and hence in the product stream. In other words, merely confirming a low amount of co-boilers in the product stream does not suggest the existence of 2,4-dimethylpentane and 2,2,3-trimethylbutane in the feed stream. Actually, there is a demand for a hydrocracking process which allows hydrocracking of substantially all co-boilers of benzene, including 2,4-dimethylpentane and 2,2,3-trimethylbutane. In other words, there is need for a process that can crack 2,4-dimethylpentane and 2,2,3-trimethylbutane, and produce chemical grade benzene.

It is an object of the present invention to provide a hydrocracking process in which above and/or other needs are met.

Accordingly, the present invention provides a hydrocracking process comprising:

contacting a hydrocracking feed stream in the presence of hydrogen with a hydrocracking catalyst under process conditions including a temperature of 425-580° C., a pressure of 300-5,000 kiloPascals (kPa) gauge and a Weight Hourly Space Velocity (WHSV) of 0.1-30 $h^{-1}$ to produce a hydrocracking product stream comprising benzene;

wherein the hydrocracking feed stream comprises $C_5$-$C_{12}$ hydrocarbons which comprise 2,4-dimethylpentane and/or 2,2,3-trimethylbutane, wherein the total amount of 2,4-dimethylpentane and 2,2,3-trimethylbutane is at least 0.5 wt % of the hydrocracking feed stream;

wherein the hydrocracking catalyst comprises a hydrogenation metal in an amount of 0.010-0.30 wt % with respect to the total catalyst; and wherein the hydrocracking catalyst comprises a medium pore zeolite having a pore size of 5-6 Å and a silica to alumina molar ratio of 20-75; preferably the hydrocracking catalyst comprises a medium pore zeolite having a pore size of 5-6 Å and a silica to alumina molar ratio of 20-75 and a large pore zeolite having a pore size of 6-8 Å and a silica to alumina molar ratio of 10-80, wherein the hydrogenation metal is deposited on the medium pore zeolite and the large pore zeolite.

It was surprisingly found that certain branched alkanes having boiling points close to the boiling points of benzene such as between 75° C. and 90° C., namely 2,4-dimethylpentane (24DMP) and 2,2,3-trimethylbutane (223TMB), cannot be effectively hydrocracked by known hydrocracking catalysts. In other words, either the conversion is less than 90% and/or the deactivation rate of the catalyst is greater than $|-2.5 \times 10^{-4}\ hr^{-1}|$. These branched alkanes which are difficult to hydrocrack are not present in large amounts in typical feed streams and therefore this problem is not recognized when using these feed streams. The recognition of the problem was possible by the present inventors by hydrocracking specific feed streams with high amounts of 24DMP and 223TMB for the purpose of generating high purity benzene and analyzing the obtained product stream. The inventors recognized this problem and found that specific hydrocracking catalyst according to the invention can solve this problem by effectively hydrocracking all benzene co-boilers including these benzene co-boilers. The absence of co-boilers of benzene in the product stream allows obtaining chemical grade benzene by simple distillation of the product stream.

It was surprisingly found that the improved conversion of these benzene co-boilers can be achieved by a catalyst comprising a hydrogenating metal and a medium pore zeolite having a silica-to-alumina ratio of 20 to 75. The hydrogenating metal could be present in greater than or equal to 0.09 wt %, preferably greater than or equal to 0.10 wt %, e.g., 0.09 to 3 wt %, or 0.10 to 2.5 wt %, based upon a total weight of the catalyst.

It was surprisingly found that the improved conversion of these benzene co-boilers can be achieved by a catalyst comprising a medium pore zeolite having a silica to alumina molar ratio of 20-75 and a hydrogenation metal deposited on the zeolite (e.g., a catalyst comprising a shaped body comprising a medium pore zeolite and a binder and a hydrogenation metal deposited on the shaped body), or by a catalyst comprising a medium pore zeolite and a large pore zeolite and a hydrogenation metal deposited on the medium pore zeolite and the large pore zeolite.

Accordingly, in some embodiments, the hydrogenation metal is deposited on a shaped body comprising the medium pore zeolite having a pore size of 5-6 Å and a silica ($SiO_2$) to alumina ($Al_2O_3$) molar ratio of 20-75 and a binder. It was found that this leads to a higher conversion of these benzene co-boilers compared to a similar catalyst where a similar amount of the hydrogenation metal is deposited on the medium pore zeolite without a binder. The zeolite in the catalyst may consist of the medium pore zeolite, or may further comprise a large pore zeolite having a pore size of 6-8 Å and a silica ($SiO_2$) to alumina ($Al_2O_3$) molar ratio of 10-80.

When the hydrocracking catalyst comprises the medium pore zeolite having a pore size of 5-6 Å and a silica to alumina molar ratio of 20-75 and also a large pore zeolite catalyst having a pore size of 6-8 Å and a silica ($SiO_2$) to alumina ($Al_2O_3$) molar ratio of 10-80 in addition to a medium pore zeolite catalyst, the hydrocracking catalyst may be in the form of powder and free from a binder. It was found that pore size (that allows the molecules to enter the zeolite pores to reach active sites), and the zeolite silica to alumina ratio (number of acid sites), and with hydrogenation metal deposited on the large pore zeolite leads to a higher conversion of the branched alkanes compared to a similar catalyst where a similar amount of the hydrogenation metal is deposited only on the medium pore zeolite.

As used herein, the term "$C_n$ hydrocarbons", wherein "n" is a positive integer, is meant to describe all hydrocarbons having n carbon atoms. Moreover, the term "$C_{n+}$ hydrocarbons" is meant to describe all hydrocarbon molecules having n or more carbon atoms. Accordingly, the term "$C_{5+}$ hydrocarbons" is meant to describe a mixture of hydrocarbons having 5 or more carbon atoms.

Hydrocracking Feed Stream

The hydrocracking feed stream comprises $C_5$-$C_{12}$ hydrocarbons including at least 0.5 wt % of 2,4-dimethylpentane and 2,2,3-trimethylbutane, based upon the total weight of the hydrocracking feed stream. The hydrocracking feed stream can comprise $C_5$-$C_{12}$ hydrocarbons including greater than or equal to 20 wt % (preferably greater than or equal to 30 wt %, or greater than or equal to 40 wt %) $C_{6+}$ non-aromatics, wherein the $C_{6+}$ non-aromatics comprise at least 0.5 wt % of 2,4-dimethylpentane and 2,2,3-trimethylbutane, based upon the total weight of the hydrocracking feed stream.

The hydrocracking feed stream is a mixture comprising $C_5$-$C_{12}$ hydrocarbons, preferably having a boiling point (b.p.) in the range of 30–195° C. Preferably, the hydrocracking feed stream mainly comprises $C_6$-$C_8$ hydrocarbons. The hydrocracking feed stream comprises 2,4-dimethylpentane (b.p. 80° C.) and 2,2,3-trimethylbutane (b.p. 81° C.). The hydrocracking feed stream may further comprise other branched alkanes having boiling points between 75° C. and 90° C. These alkanes include 2,2-dimethylpentane (b.p. 78° C.), 3,3-dimethylpentane (b.p. 86° C.), 2,3-dimethylpentane (b.p. 89° C.) and 2-methylhexane (b.p. 90° C.).

The amount of the branched alkanes having boiling points between 75° C. and 90° C. (i.e., benzene co-boiler branched alkanes) in the hydrocracking feed stream may be at least 0.5 wt %, at least 1.0 wt %, at least 2.0 wt %, or at least 5.0 wt %, with respect to total hydrocarbon feed. The amount of the branched alkanes having boiling points between 75° C. and 90° C. may be at most 15 wt %, or at most 10 wt %.

The total amount of 2,4-dimethylpentane and 2,2,3-trimethylbutane in the hydrocracking feed stream may be at least 0.5 wt %, at least 1.0 wt %, at least 2.0 wt %, or at least 5.0 wt %, with respect to total hydrocarbon feed. The total amount of 2,4-dimethylpentane and 2,2,3-trimethylbutane may be at most 15 wt %, or at most 10 wt %, with respect to total hydrocarbon feed.

The amount of 2,4-dimethylpentane in the hydrocracking feed stream may be at least 0.5 wt %, at least 1.0 wt %, at least 2.0 wt %, or at least 5.0 wt %, with respect to total hydrocarbon feed. The amount of 2,4-dimethylpentane may be at most 15 wt %, or at most 10 wt %, with respect to total hydrocarbon feed.

The amount of 2,2,3-trimethylbutane in the hydrocracking feed stream may be at least 0.5 wt %, at least 1.0 wt %, at least 2.0 wt %, or at least 5.0 wt %, with respect to total hydrocarbon feed. The amount of 2,2,3-trimethylbutane may be at most 15 wt %, or at most 10 wt %, with respect to total hydrocarbon feed.

Some types of feed streams may include such high amounts of benzene co-boiler branched alkanes (e.g., 2,4-dimethylpentane and/or 2,2,3-trimethylbutane). Naphtha derived from natural gas condensate (e.g., Saudi A-180, Texas shale gas condensate, etc.), pygas naphtha (benzene-rich naphtha derived from the liquid byproduct of a steam cracker), straight run naphtha from distillation of crude oil, naphtha from cracking processes (e.g. FCC, hydrocracking), and raffinate from reformate, may have various compositions, and some may have such high amounts of benzene co-boiler branched alkanes (e.g., 2,4-dimethylpentane and/or 2,2,3-trimethylbutane). It is noted that only certain types of these feed streams have such high amounts of benzene co-boiler branched alkanes, such as 2,4-dimethylpentane and/or 2,2,3-trimethylbutane.

In some embodiments, the feed stream used in the process of the present invention has been depentanised. Preferably, the feed stream comprises at most 5 wt % of $C_5$ hydrocarbons, more preferably at most 4 wt %, at most 3 wt %, at most 2 wt %, at most 1 wt %, or $C_5$ hydrocarbons.

Preferably, the hydrocracking feed stream is provided by a process which does not involve the step of removing benzene or removing $C_6$ hydrocarbons. This means that intentional removal of benzene has not been performed in providing the hydrocracking feed stream or the fresh feed stream. The step of removing benzene typically induces the removal of co-boilers of benzene. According to the present invention, the benzene co-boilers present in the hydrocracking feed stream are advantageously converted to useful LPG.

Preferably, the hydrocracking feed stream may comprise at least 5 wt % of benzene, for example at least 10 wt % of benzene, at least 20 wt % of benzene, at least 30 wt % of benzene or at least 40 wt % of benzene, and/or at most 90 wt % of benzene, for example at most 80 wt %, at most 70 wt %, at most 60 wt % or at most 50 wt % of benzene.

The hydrocracking feed stream contains $C_5$-$C_{12}$ hydrocarbons. For example, the hydrocracking feed stream contains aromatics and nonaromatics. The aromatics include at least one of benzene, toluene, and xylene. The aromatics can be present in an amount of greater than or equal to 40 wt %, e.g., greater than or equal to 50 wt %, or greater than or equal to 60 wt %, or even greater than or equal to 70 wt %, based upon a total weight of the feed stream. The hydrocracking feed stream is contacted in the presence of hydrogen in a hydrocracking reactor with the hydrocracking catalyst of the invention.

According to the process of the present invention, a hydrocracking feed stream comprising a relatively large amount of certain branched alkanes which are difficult to hydrocrack is efficiently converted into a mixture comprising substantially no co-boilers of benzene (e.g., less than or equal to 0.2 wt %). As a result thereof, chemical grade BTX or chemical grade benzene is obtained by relatively simple separation methods such as gas-liquid separation or distillation. The product produced by the hydrocracking step of the process of the present invention (hydrocracking product stream) comprises LPG, BTX and methane.

The term "LPG" as used herein refers to the well-established acronym for the term "liquefied petroleum gas". LPG generally consists of a blend of $C_2$-$C_4$ hydrocarbons i.e. a mixture of $C_2$, $C_3$, and $C_4$ hydrocarbons.

The term "BTX" as used herein is well known in the art and relates to a mixture of benzene, toluene and xylenes.

As used herein, the term "chemical grade BTX" relates to a hydrocarbon mixture comprising less than 5 wt % hydrocarbons other than benzene, toluene and xylenes, preferably less than 4 wt % hydrocarbons other than benzene, toluene and xylenes, more preferably less than 3 wt % hydrocarbons other than benzene, toluene and xylenes, and most preferably less than 2.5 wt % hydrocarbons other than benzene, toluene and xylenes.

Furthermore, the "chemical grade BTX" produced by the process of the present invention comprises less than 1 wt % non-aromatic $C_{6+}$ hydrocarbons, preferably less than 0.7 wt % non-aromatic $C_{6+}$ hydrocarbons, more preferably less than 0.5 wt % non-aromatic $C_{6+}$ hydrocarbons and most preferably less than 0.2 wt % non-aromatic $C_{6+}$ hydrocarbons.

As used herein, the term "chemical grade benzene" relates to a hydrocarbon stream comprising less than or equal to 0.2 wt % hydrocarbons other than benzene.

The term "aromatic hydrocarbon" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons.

The hydrocracking product stream produced in the process of the present invention preferably comprises less than 5 wt % of methane. Preferably, the hydrocracking product stream produced in the process of the present invention comprises less than 4 wt % of methane, more preferably less than 3 wt % methane, even more preferably less than 2 wt % methane, even more preferably less than 1.5 wt % methane, even more preferably less than 1.4 wt % methane, even more preferably less than 1.3 wt % methane, even more preferably less than 1.2 wt % methane, even more preferably less than 1.1 wt % methane, and most preferably less than 1 wt % methane.

Preferably, the hydrocracking product stream is also substantially free from $C_5$ hydrocarbons. As meant herein, the term "hydrocracking product stream substantially free from $C_5$ hydrocarbons" means that said hydrocracking product stream comprises less than 1 wt % $C_5$ hydrocarbons, preferably less than 0.7 wt % $C_5$ hydrocarbons, more preferably less than 0.6 wt % $C_5$ hydrocarbons and most preferably less than 0.5 wt % $C_5$ hydrocarbons.

Process Conditions

The process conditions under which the hydrocracking of the feed stream is performed are an important determinant for the composition of the hydrocracking product stream.

In general, when the space velocity is too high, not all co-boilers of BTX are hydrocracked, so it will not be possible to obtain a chemical grade BTX by simple distillation of the product stream. However, at too low space velocity the yield of methane rises at the expense of ethane, propane and butane. Also, a higher space velocity requires smaller reactor volumes and thus a lower CAPEX. Hence, it is advantageous to perform the process of the invention at a high space velocity at which substantially all co-coilers of BTX are hydrocracked.

It was found that the hydrocracking step (b) can advantageously be performed at a high space velocity while allowing substantially all co-boilers of BTX to be hydrocracked, due to the high activity of the catalyst.

Accordingly, in some preferred embodiments, the step (b) is performed at a Weight Hourly Space Velocity (WHSV) of 0.1-30 per hour ($hr^{-1}$), for example at least 1 $hr^{-1}$, at least 2 $hr^{-1}$, at least 3 $hr^{-1}$, at least 5 $hr^{-1}$, at least 6 $hr^{-1}$, at least 7 $hr^{-1}$ or at least 8 $hr^{-1}$, and/or at most 25 $hr^{-1}$, at most 20 $hr^{-1}$, at most 15 $hr^{-1}$, at most 10 $hr^{-1}$, or at most 9 $hr^{-1}$. High WHSV such as at least 8 $hr^{-1}$ allows particularly small reactor volumes and lower capital expenditure (CAPEX).

It has also been found that step (b) can be operated at a relatively low temperature. This allows for greater operational flexibility as well as lower heat duty and may allow longer cycle lengths. Accordingly, in some preferred embodiments, the step (b) is performed at a temperature of 425-445° C. In other embodiments, the step (b) is performed at a temperature of 450-580° C. The higher temperature range results in a high hydrocracking conversion rate.

The hydrocracking of the feed stream is performed at a pressure of 300-5,000 kPa gauge, more preferably at a pressure of 600-3,000 kPa gauge, particularly preferably at a pressure of 1,000-2,000 kPa gauge and most preferably at a pressure of 1200-1600 kPa gauge. By increasing reactor pressure, conversion of $C_{5+}$ non-aromatics can be increased, but higher pressure also increases the yield of methane and the hydrogenation of aromatic rings to cyclohexane species which can be cracked to LPG species. This results in a reduction in aromatic yield as the pressure is increased and, as some cyclohexane and its isomer methylcyclopentane are not fully hydrocracked, a pressure of 1,200-1,600 kPa may result in a high purity of the resultant benzene.

The hydrocracking step is performed in the presence of an excess of hydrogen in the reaction mixture. This means that a more than stoichiometric amount of hydrogen is present in the reaction mixture that is subjected to hydrocracking. Preferably, the molar ratio of hydrogen to hydrocarbon species ($H_2$/HC molar ratio) in the reactor feed is between 1:1 and 4:1, preferably between 1:1 and 3:1 and most preferably between 2:1 and 3:1. A higher benzene purity in the product stream can be obtained by selecting a relatively low $H_2$/HC molar ratio. In this context the term "hydrocarbon species" means all hydrocarbon molecules present in the reactor feed such as benzene, toluene, hexane, cyclohexane, etc. The composition of the feed and/or the volumetric flow of the hydrocarbon stream as a vapor, are used to calculate the average molecular weight of this stream to be able to calculate the correct hydrogen feed rate. The excess amount of hydrogen in the reaction mixture suppresses the coke formation which is believed to lead to catalyst deactivation.

Catalyst

The hydrocracking catalyst used in the process of the present invention comprises a hydrogenation metal. The hydrocracking catalyst further comprises a medium pore zeolite having a pore size of 5-6 Angstroms (Å) and a silica ($SiO_2$) to alumina ($Al_2O_3$) molar ratio of 20 to 75.

In some embodiments, the hydrogenation metal is deposited on a shaped body comprising the medium pore zeolite and a binder. The shaped body may further comprise a large pore zeolite having a pore size of 6-8 Å and a silica ($SiO_2$) to alumina ($Al_2O_3$) molar ratio of 10 to 80.

Examples of the shaped bodies include, but are not limited to, spherically or cylindrically shaped pellets, tablets, particles and extrudates. The shaped body typically has an average diameter of about 0.1 millimeter (mm) to about 7 mm, typically 1.4 mm to 3.5 mm. The diameter is usually measured by slide caliper. The shaped body typically has an average length of 3 to 8 mm. The average as used herein is an arithmetic average. One specific example of the shaped body is cylindrically shaped extrudates with an average diameter of about 1.6 mm (1/16 inch) with an average length of extrudates about 3 to 8 mm. In such catalyst, the distance between the hydrogenation metal and the zeolite acid site is less than that in a mixed catalyst of a shaped zeolite body and hydrogenation metal supported on a binder. An example of the latter would be a mixture of ZSM-5 zeolite extrudates and Pt deposited on shaped $Al_2O_3$.

In some embodiments, the hydrocracking catalyst may be in the form of powder and free from a binder. In this case, the hydrocracking catalyst further comprises a medium pore zeolite having a pore size of 5-6 Å and a silica ($SiO_2$) to alumina ($Al_2O_3$) molar ratio of 20-75 and a large pore zeolite having a pore size of 6-8 Å and a silica ($SiO_2$) to alumina ($Al_2O_3$) molar ratio of 10-80. The hydrogenation metal and optionally La and/or Ga are deposited on the medium pore zeolite and the large pore zeolite.

Zeolite

The hydrocracking catalyst used according to the invention comprises a medium pore zeolite having a pore size of 5-6 Å. The hydrocracking catalyst used according to the invention may further comprise a large pore zeolite having a pore size of 6-8 Å. The terms "medium pore zeolite" and "large pore zeolite" are commonly used in the field of zeolite catalysts.

Zeolites are well-known molecular sieves having three dimensional structures with well-defined channels, pores, cavities with defined pore size. As used herein, the term "zeolite" or "aluminosilicate zeolite" relates to an aluminosilicate molecular sieve. An overview of their characteristics is for example provided by the chapter on Molecular Sieves in Kirk-Othmer Encyclopedia of Chemical Technology, Volume 16, p 811-853; in Atlas of Zeolite Framework Types, 5th edition, (Elsevier, 2001). In this Atlas of Zeolite Framework Types, various zeolites are listed based on ring structure. Zeolites of the 8-ring structure type are called small pore zeolites.

Preferably, the zeolite present in the catalyst is in a hydrogen form or a $NH_4$-form, i.e. having at least a portion of the original cations associated therewith replaced by $H^+$ ions or $NH_4^+$ ions, respectively. Various methods to convert an aluminosilicate zeolite to the hydrogen form can be used. A first method involves direct treatment employing an acid, for example a mineral acid ($HNO_3$, HCl, etc.). A second method involves direct exchange using an ammonium salt (e.g. $NH_4NO_3$) followed by calcination. The zeolite can optionally contain up to trace levels of other cations such as Na (wherein a trace level is at most 0.05 wt % based upon the total weight of the zeolite).

Possible zeolites include, but are not limited to, ZSM-5, MCM-22, ZSM-11, beta zeolite, EU-1 zeolite, faujasite (zeolite Y), ferrierite and mordenite.

Possible medium pore zeolites are 10-ring zeolites, i.e. the pore is formed by a ring consisting of 10 tetrahedra of $[SiO_4]$ and $[AlO_4]^-$. The negative charge arising from $[AlO_4]^-$ is neutralized by a cation in the zeolite. Preferably, the medium pore zeolite is a ZSM-5 zeolite.

The silica ($SiO_2$) to alumina ($Al_2O_3$) molar ratio of the medium pore zeolite is in the range of 20-75. This shows the optimum catalyst hydrocracking performance to obtain desired benzene purity from a feedstock containing benzene co-boilers. Means and methods for quantifying the $SiO_2$ to $Al_2O_3$ molar ratio of a zeolite include, but are not limited to AAS (Atomic Absorption Spectrometer), ICP (Inductively Coupled Plasma Spectrometry) analysis, and XRF (X-ray fluorescence). It is noted that the $SiO_2$ to $Al_2O_3$ molar ratio referred herein is meant as the ratio in the zeolite prior to being mixed with the other components. Preferably, the $SiO_2$ to $Al_2O_3$ molar ratio is measured by XRF.

Preferably, the silica to alumina molar ratio of the medium pore zeolite is in the range of 20-50. At such ratio, the hydrocracking of the benzene co-boilers is especially efficient. Even more preferably, the silica to alumina molar ratio of the medium pore zeolite is in the range of 20-30 or 21-29. At such ratio, the resistance of the catalyst to catalyst deactivation is high.

In some embodiments, the zeolite present in the catalyst consists of the medium pore zeolite. In other embodiments, the hydrocracking catalyst is a combination of the medium pore zeolite and the large pore zeolite.

Suitable large pore zeolites are 12-ring zeolites. Preferably, the large pore zeolite includes at least one of Y zeolite, beta zeolite, and mordenite.

The silica ($SiO_2$) to alumina ($Al_2O_3$) molar ratio of the large pore zeolite is in the range of 5 to 100, for example 10 to 80, preferably 10 to 60.

Preferably, the zeolite in the hydrocracking catalyst comprises 70-100 wt % of the medium pore zeolite and 0-30 wt % of the large pore zeolite, for example 75-95 wt % of the medium pore zeolite and 5-25 wt % of the large pore zeolite, or 75-85 wt % of the medium pore zeolite and 15-25 wt % of the large pore zeolite, with respect to the total amount of the zeolite.

Hydrogenation Metal

Preferably, the hydrogenation metal is at least one element selected from Group 10 of the periodic table of Elements, rhodium, and iridium. The preferred Group 10 elements are palladium and platinum, particularly platinum. In other words, the hydrogenation metal can consist of platinum. Optionally, the hydrocracking catalyst can be free of metals other than the Group 10 metals of the Periodic Table of Elements, rhodium, and iridium; preferably free of metals other than palladium and platinum. As used herein "free of metals" means that no other metals were added to the hydrocracking catalyst.

Binder

In some embodiments, the catalyst comprises a binder. The binder material can be an inorganic oxide material. The binder material can comprise an aluminum-containing or silicon-containing material such as silica, alumina, clay, aluminum phosphate, silica-alumina, or combinations comprising at least one of the foregoing. Alumina ($Al_2O_3$) is the preferred binder. The catalyst can comprise up to 99 wt %, e.g., 1 to 99 wt %, for example 10 to 90 wt %, 10 to 50 wt % or 20 to 40 wt % of the binder based on the total weight of the catalyst.

Preferably, the binder has been treated with a mineral acid such as nitric acid, hydrochloric acid, phosphoric acid, or sulfuric acid, preferably nitric acid. Treating the binder with a mineral acid improves physical strength of the formed catalyst.

It will be appreciated that materials such as SiC used for diluting the catalyst before loading to the reactor are not considered as a binder and is not part of the catalyst.

Metal Amount

The catalyst according to the process of the present invention comprises 0.010-0.30 wt. % of the hydrogenating metal. In the context of the present invention, the term "wt %" when relating to the metal content as comprised in a catalyst relates to the wt % of said metal in relation to the total weight of the catalyst. The amount of the hydrogenating metal in the catalyst can be determined e.g. by subjecting the catalyst to XRF or ICP.

Even more preferably, the catalyst comprises at least 0.030 wt %, at least 0.050 wt %, at least 0.075 wt %, at least 0.10 wt %, at least 0.125 wt % or at least 0.20 wt %, of the hydrogenating metal in relation to the total weight of the catalyst. At such amount, the resistance of the catalyst to catalyst deactivation is high. The catalyst may comprise at most 0.275 wt % of the hydrogenating metal in relation to the total weight of the catalyst.

The hydrocracking catalyst may further comprise La and/or Ga. The total amount of La and/or Ga may be 0.10-0.40 wt % of the total weight of the catalyst. However, in some embodiments, the hydrocracking catalyst does not comprise La and Ga, i.e. comprises less than 0.01 parts Ga and less than 0.01 parts, preferably comprises less than 0.005 parts Ga and less than 0.005 parts (on the basis of 100 parts by weight of total catalyst).

Desirably, the hydrocracking catalyst has a sufficient hydrogenation activity to hydrogenate unsaturated non-aromatic hydrocarbons. Accordingly, it is preferred that the catalyst does not comprise secondary metals, such as tin, lead, or bismuth that inhibit the hydrogenation activity of the hydrogenation metal. Preferably, the hydrocracking catalyst comprises less than 0.01 parts tin and less than 0.02 parts lead and less than 0.01 parts bismuth (on the basis of 100 parts by weight of the total catalyst), preferably less than 0.005 parts tin and less than 0.01 parts lead and less than 0.005 parts bismuth (on the basis of 100 parts by weight of total catalyst).

Further, preferably, the hydrocracking catalyst can comprise less than 0.01 parts molybdenum (on the basis of 100 parts by weight of the total catalyst).

Process for Preparation of Catalyst

The catalyst may be made by depositing the hydrogenation metal (and optionally La and/or Ga) on the zeolite for preparing a catalyst in powder form. The catalyst may also be made by depositing the hydrogenation metal (and optionally La and/or Ga) on the shaped body comprising the zeolite and the binder, e.g. by a wet or vapor phase impregnation or by an ion-exchange method. Examples of the preparation method for the catalyst wherein the hydrogenation metal is Pt uses $(NH_3)_4Pt(NO_3)_2$, $(NH_3)_4PtCl_2$ or $(NH_3)_4Pt(OH)_2$ as a platinum source usually in combination with $NH_4C_1$. Another example of the preparation method for the catalyst wherein the hydrogenation metal is Pt uses $H_2PtCl_6$ as a platinum source. The method wherein $H_2PtCl_6$ is used as the platinum source may be preferable in that $NH_4Cl$ is not needed.

The feed stream is cracked by the catalyst to produce a hydrocracking product stream comprising LPG and BTX. The process may further comprise separating BTX or benzene from the hydrocracking product stream. The hydrocracking product stream may be subjected to separation by standard means and methods suitable for separating methane and unreacted hydrogen comprised in the hydrocracking product stream as a first separate stream, the LPG comprised in the hydrocracking product stream as a second separate stream and BTX as a third separate stream. Preferably, the stream comprising BTX is separated from the hydrocracking product stream by gas-liquid separation or distillation. Benzene may be further separated from the stream comprising BTX.

One non-limiting example of such a separation method of the hydrocracking product stream includes a series of distillation steps. The first distillation step at moderate temperature is to separate most of the aromatic species (liquid product) from the hydrogen, $H_2S$, methane and LPG species. The gaseous stream from this distillation is further cooled (to about −30° C.) and distilled again to separate the remaining aromatic species and most of the propane and butane. The gaseous product (mainly hydrogen, $H_2S$, methane, and ethane) is then further cooled (to about −100° C.) to separate the ethane and leave the hydrogen, $H_2S$ and methane in the gaseous stream that will be recycled back to the hydrocracking reactor. To control the levels of $H_2S$ and methane in the reactor feed, a proportion of this recycle gas stream is removed from the system as a purge. The quantity of material that is purged depends on the levels of methane and $H_2S$ in the recycle stream which in-turn depend on the feed composition. As the purge will contain mainly hydrogen and methane it is suitable for use as a fuel gas or may be further treated (e.g. via a pressure swing adsorption unit) to separately recover a high purity hydrogen stream and a methane/$H_2S$ stream which can be used as a fuel gas.

In a further embodiment, the present invention relates to a process for producing benzene from a feed stream comprising $C_5$-$C_{12}$ hydrocarbons, wherein the said process comprises the hydrocracking process further comprising separating BTX or benzene from the hydrocracking product stream, further comprising the step of contacting BTX (or only the toluene and xylenes fraction of said BTX produced) with hydrogen under conditions suitable to produce a hydrodealkylation product stream comprising benzene and fuel gas.

The conditions suitable to produce a hydrodealkylation product stream comprising benzene and fuel gas are well-known and are described in detail e.g. in WO2013/182534, incorporated herein by reference.

Processes for hydrodealkylation of hydrocarbon mixtures comprising $C_6$-$C_9$ aromatic hydrocarbons include thermal hydrodealkylation and catalytic hydrodealkylation; see e.g. WO 2010/102712 A2. Catalytic hydrodealkylation is preferred as this hydrodealkylation process generally has a higher selectivity towards benzene than thermal hydrodealkylation. Preferably catalytic hydrodealkylation is employed, wherein the hydrodealkylation catalyst is selected from supported chromium oxide catalyst, supported molybdenum oxide catalyst, platinum on silica or alumina and platinum oxide on silica or alumina.

The process conditions useful for hydrodealkylation, also described herein as "hydrodealkylation conditions", can be easily determined by the person skilled in the art. The process conditions used for thermal hydrodealkylation are for instance described in DE 1668719 A1 and include a temperature of 600-800° C., a pressure of 3-10 MPa gauge and a reaction time of 15-45 seconds. The process conditions used for the preferred catalytic hydrodealkylation preferably include a temperature of 500-650° C., a pressure of 3.5-7 MPa gauge and a Weight Hourly Space Velocity of 0.5-2 $h^{-1}$; see also Handbook of Commercial Catalysts: Heterogeneous Catalysts ed. Howard F. Rase (2000) Loc. cit.

The hydrodealkylation product stream can be separated into a liquid stream (containing benzene and other aromatics species) and a gas stream (containing hydrogen, $H_2S$, methane, and other low boiling point hydrocarbons) by a combination of cooling and distillation. The liquid stream may be further separated, by distillation, into a benzene stream, a $C_7$ to $C_9$ aromatics stream and a heavy aromatic stream. The $C_7$ to $C_9$ aromatic stream, or some part of it, may be fed back to reactor section as a recycle to increase overall conversion and benzene yield. The heavy aromatic stream, which contains polyaromatic species such as biphenyl, is preferably not recycled to the reactor but may be exported as a separate product stream. The gas stream contains significant quantities of hydrogen and may be recycled back, via a recycle gas compressor, to the reactor section. A recycle gas purge may be used to control the concentrations of methane and $H_2S$ in the reactor feed.

The invention is now elucidated by way of the following examples, without however being limited thereto.

EXAMPLES

Below table shows the analyzed composition of a pygas (Platfiner) stream. It can be understood that this pygas comprises essentially no amount of hydrocarbons having a boiling point close to benzene except for cyclohexane, methylcyclopentane (MCP) and 1,3-dimethylcyclopentane (1,3-DMCP). It comprises no detectable amount of 2,4-dimethylpentane (BP 80° C.) or 2,2,3-trimethylbutane (BP 81° C.).

Pygas Composition (Platfiner)

| Component | C Number | BP, ° C. | wt % |
|---|---|---|---|
| butane | 4 | −1 | 0.02 |
| methylbutane | 5 | 27.7 | 0.34 |
| pentane | 5 | 36.1 | 0.39 |
| 2-methylpentane | 6 | 60 | 3.93 |
| 3 methylpentane | 6 | 63 | 2.58 |
| hexane | 6 | 68 | 7.59 |
| methylcyclopentane | 6 | 72 | 7.98 |
| benzene | 6 | 80.1 | 47.87 |
| cyclohexane | 6 | 80.7 | 3.24 |
| trans 1,3-dimethylcyclopentane | 7 | 91 | 0.47 |

-continued

| Component | C Number | BP, ° C. | wt % |
|---|---|---|---|
| 1,3-dimethylcyclopentane | 7 | 92 | 1.15 |
| 2,2,4-trimethylpentane | 7 | 98 | 0.37 |
| heptane | 7 | 98 | 0.80 |
| methylcyclohexane | 7 | 101 | 0.57 |
| ethylcyclopentane | 7 | 103 | 0.66 |
| toluene | 7 | 111 | 13.59 |
| octane | 8 | 126 | 0.05 |
| ethylbenzene | 8 | 136 | 3.07 |
| m/p-xylene | 8 | 139/140 | 1.41 |
| o-xylene | 8 | 144 | 0.44 |
| nonane | 9 | 151 | 0.05 |
| iso propyl benzene | 9 | 152 | 0.04 |
| propyl benzene | 9 | 159 | 0.01 |
| 1-methyl-(3&4)-ethylbenzene | 9 | 152 | 0.06 |
| 1,3,5-trimethylbenzene | 9 | 163-166 | 0.01 |
| 1-methyl 2-ethyl benzene | 9 | 152 | 0.01 |
| pseudocumene | 9 | 168.5 | 0.02 |
| indane | 9 | 176.5 | 0.01 |
| butyl benzene | 10 | 183 | 0.01 |
| 1,3-diethyl benzene | 10 | 182 | 0.01 |

Reactor and Catalyst Test Conditions

Referring to Experiments 1 to 5, the hydrocracking of a hydrocarbon feed stream employing catalysts described in this application were performed using stainless steel tube reactor as described below. 0.5 grams (g) of catalyst (sized 20-40 mesh) was diluted to 4 milliliters (ml) by premixing with SiC (30 grit) and was loaded in a reactor.

Reactor description: ⅜ inch (") inch tube, 0.035" wall thickness. ⅛" thermocouple with a ¼" spacer bar; 12"×1" aluminum over-sleeve; reactor bed is approximately 4 inches in length in the center of the sleeve.

The catalyst was pre-activated (drying, Pt reduction) by subjecting it to 100 standard cubic centimeters (sccm) of $H_2$ per minute at 130° C. under 50 pounds per square inch gauge (psig) for 2 hours and subsequently the temperature was raised to 350° C. (at 50 psig) for reduction under 200 sccm of $H_2$ (with 50 parts per million by weight (ppm) of $H_2S$) for 30 min.

Hereinafter, standard feed refers to a feed consisting of 70 wt % benzene, 15 wt % methylcyclopentane and 15 wt % 3-methylpentane. In all Experiments 1 to 5, the standard feed was first introduced to the reactor containing specific catalyst at hydrocracking reaction conditions as described below and continued for a minimum of 15 hours to establish a steady cracking activity. Subsequently, the standard feed was replaced by the feed containing a specific branched hydrocarbon as described for each experiment. All components of the hydrocracking feed stream are Aldrich regent grade chemicals dried under 4 A molecular sieves overnight.

The standard feed was introduced to the reactor at a temperature of 470° C. and a pressure of 200 psig. The molar ratio of $H_2$ to the hydrocarbons was 4 to 1, and the $H_2S$ content was 50 ppm based on the total hydrocarbon and $H_2$ feed. In all experiments, the same WHSV was maintained.

Experiment 1

Feeds were prepared by adding one of the compounds shown in Table 1 (hydrocarbons having boiling point of 75 to 90° C.) to a feed containing benzene, methylcyclopentane (MCP) and 3-methylpentane (3MP). The resulting feeds contained 70 wt % benzene, 15 wt % methylcyclopentane (MCP), 10 wt % 3-methylpentane (3MP), and 5 wt % of one of the compounds shown in Table 1. In each of examples (column 1 in Table 1), after initial stable activity with the standard feed, each of the feeds containing 5 wt % of one of the components (column 1 in Table 1) was subjected to hydrocracking at 470° C., about WHSV 10/h and 200 psig.

The feed stream contains $H_2$ ($H_2$/HC molar 4) and 50 ppm S (fed $H_2S$). The hydrocracking catalyst used was a powder catalyst of ZSM-5 deposited with Pt (no binder), wherein the amount of Pt was 0.03 wt % of the total catalyst and the silica to alumina molar ratio of the ZSM-5 was 50.

The result of the conversion is shown in Table 1. It can be seen that the conversion of 2,4-dimethylpentane (24DMP) and 2,2,3-trimethylbutane (223TMB) is low, e.g., under 80% and under 30% conversion respectively. It can be understood that it is difficult to obtain a product stream with substantially no benzene co-boilers from a feed stream comprising large amounts of 24DMP and/or 223TMB, while other hydrocarbons can be substantially completely converted.

TABLE 1

| Nonaromatics | Carbon # | b.p., ° C. | % Conversion |
|---|---|---|---|
| 2,2-dimethylpentane | 7 | 78 | 100.0 |
| 2,4-dimethylpentane | 7 | 80 | 78.3 |
| 2,2,3-trimethylbutane | 7 | 81 | 27.7 |
| 2,3-dimethylpentane | 7 | 89 | 99.7 |
| 2-methylhexane | 7 | 90 | 100 |
| cyclohexane | 6 | 81 | 99.4 |

Experiment 2: Effect of Extrudate vs Powder on 223TMB Cracking

In each of the examples, after initial stable activity with the standard feed, a feed containing 70 wt % benzene, 15 wt % methylcyclopentane (MCP), 10 wt % 3-methylpentane (3MP) and 5 wt % of 2,2,3-trimethylbutane (223TMB) was subjected to hydrocracking at 470° C., about WHSV 10/h and 200 psig. The feed stream contains $H_2$ ($H_2$/HC molar 4) and 50 ppm S (fed $H_2S$).

In CEx 1-2, the catalysts used were a Pt deposited ZSM-5 powder catalyst with no binder. In Ex 3-5, the catalysts used were in the form of an extrudate of ZSM-5 and alumina on which Pt was deposited. The silica-to-alumina molar ratio of the ZSM-5 is 50. The amount of Pt in the catalyst is shown in Table 2.

TABLE 2

| | Catalyst | | 223TMB conversion | | |
|---|---|---|---|---|---|
| | | | | Averaged | |
| Example | Pt on | Pt (wt %) | Conversion (%) | during tos (h) | Deactivation rate[1] (hr$^{-1}$) |
| CEx1 | ZSM-5 powder | 0.032 | 27.7 | 30-79 | not estimated |
| CEx2 | ZSM-5 powder | 0.102 | 36.5 | 56-71 | not estimated |
| Ex3 | ZSM-5 extrudates | 0.067 | 52.7 | 30-48 | $|-4.2 \times 10^{-3}|$ |
| Ex4 | ZSM-5 extrudates | 0.15 | 74.6 | 50-60 | $|-6.1 \times 10^{-3}|$ |
| Ex5 | ZSM-5 extrudates | 0.25 | 83.7 | 52-70 | $|-3.4 \times 10^{-3}|$ |

[1]Deactivation rate: absolute value of the decrease of % conversion of 223TMB per hour calculated during time-on-stream (tos) is indicated.

It can be understood that an increased amount of Pt shows an increase in the conversion of 223TMB for both the powder form and the extrudate form. However, the extrudate shows a higher conversion than the powder even at a low Pt content (comparison of CEx2 with 0.102 wt % Pt vs Ex3 with 0.067 wt % Pt). It can be concluded that the extrudate shows a better conversion than the powder at the same Pt content.

Experiment 3: Effect of Large Pore Zeolite on 24DMP Cracking

In each of the examples, after initial stable activity was achieved with the standard feed, a feed containing 70 wt % benzene, 15 wt % methylcyclopentane (MCP), 10 wt % 3-methylpentane (3MP), and 5 wt % of 24DMP was subjected to hydrocracking at 470° C., about WHSV 10/h and 200 psig. The feed stream contained $H_2$ ($H_2$/HC molar 4) and 50 ppm S (fed $H_2S$).

In CEx 6-7, the catalysts used were a Pt deposited ZSM-5 powder catalyst with no binder. In Ex 8-11, the catalysts used were in the form of a physical mixture of a Pt deposited ZSM-5 powder catalyst and a Pt deposited large pore zeolite powder catalyst. The silica-to-alumina molar ratio of the ZSM-5 is 50. The silica-to-alumina molar ratio of the large pore zeolites are shown in Table 3. The amounts of Pt in the catalyst are shown in Table 3.

TABLE 3

| | Zeolite Catalyst | | | 24DMP conversion | | |
|---|---|---|---|---|---|---|
| Example | Description | | Pt, wt %, in mixed zeolite[2] | % conv | avgd during tos (h) | Deactivation rate[1] (hr$^{-1}$) |
| CEx 6 | 100 wt % of Pt(0.03%)/ZSM-5 | | 0.03 | 78.3 | 31-82 | $|-3.3 \times 10^{-4}|$ |
| CEx 7 | 100 wt % of Pt(0.097%)/ZSM-5 | | 0.097 | 93.9 | 29-48 | $|-4.9 \times 10^{-4}|$ |
| Ex 8 | 80 wt % of Pt(0.04%)/ZSM-5, SAR 50 | 20 wt % of Pt(0.094%)/HY, SAR 60 | 0.051 | 92.3 | 18-87 | $|-2.0 \times 10^{-4}|$ |
| Ex 9 | 80 wt % of Pt(0.04%)/ZSM-5, SAR 50 | 20 wt % of Pt(0.096%)/HY, SAR 30 | 0.051 | 93.3 | 17-45 | $|-0.96 \times 10^{-4}|$ |
| Ex 10 | 80 wt % of Pt(0.04%)/ZSM-5, SAR 50 | 20 wt % of Pt(0.11%)/Beta, SAR 20 | 0.054 | 98.1 | 200-255 | $|-1.7 \times 10^{-5}|$ |
| Ex 11 | 80 wt % of Pt(0.04%)/ZM-5, SAR 50 | 20 wt % of Pt(0.102%)/Mordenite, SAR 20 | 0.052 | 99 | 17-39 | no apparent deactivation |

SAR = silica ($SiO_2$) to alumina ($Al_2O_3$) molar ratio
[1]Deactivation rate: absolute value of the decrease of % conversion of 24DMP per hour calculated during time-on-stream (tos) indicated.
[2]Estimated from Pt contents in ZSM-5 and the other large pore zeolite.

The mixtures of a medium pore zeolite catalyst and a large pore zeolite catalyst show a high conversion rate of more than 92% at Pt content of 0.051 wt %. From CEx6 and CEx7, a catalyst without a large pore zeolite having a Pt content of 0.051 wt % can be estimated to have a conversion of 83.2% from the relationship between the Pt content and the conversion. It is further noted that the catalyst containing a mixture of a large pore zeolite catalyst and a medium pore zeolite catalyst had nearly half the amount of hydrogenating metal yet attained a conversion of 24DMP of greater than 90%. It can be concluded that a catalyst containing a mixture of a large pore zeolite catalyst and a medium pore zeolite catalyst shows an unexpectedly better conversion than a catalyst containing only medium pore zeolite catalyst, and the deactivation was slower. For deactivation rate, the absolute values of the rate are compared. The larger the absolute value of the deactivation rate, the faster the catalyst deactivates.

Experiment 4: Effect of Silica-to-Alumina Ratio (SAR) on 24DMP Cracking

In each of examples, after initial stable activity with the standard feed, a feed containing 70 wt % benzene, 15 wt % methylcyclopentane (MCP), 10 wt % 3-methylpentane (3MP), and 5 wt % of 24DMP was subjected to hydrocracking at 470° C., about WHSV 10/h and 200 psig. The feed stream contains $H_2$ ($H_2$/HC molar 4) and 50 ppm S (fed $H_2S$). The hydrocracking catalysts comprised Pt deposited ZSM-5 powder catalyst with no binder. The amount of Pt and the silica-to-alumina ratio of the ZSM-5 are summarized in Table 4. The result of the conversion is shown in Table 4.

TABLE 4

| | | | | 24DMP Conversion | |
|---|---|---|---|---|---|
| Example | $SiO_2/Al_2O_3$ | Pt (wt %) | % conv | averaged during tos (h) | Deactivation rate[1] ($hr^{-1}$) |
| REx12 | 80 | 0.094 | 62.9 | 32-100 | $|-7.6 \times 10^{-4}|$ |
| REx13 | 50 | 0.097 | 94.0 | 29-48 | $|-4.9 \times 10^{-4}|$ |
| REx14 | 30 | 0.099 | 98.6 | 27-43 | not observed |
| REx15 | 23 | 0.101 | 99.6 | 28-100 | not observed |

[1]Deactivation rate: absolute value of the decrease of % conversion per hour calculated during time-on-stream (tos) indicated.

The comparison of Reference Experiments 12-15 shows that a lower molar ratio of silica to alumina led to a higher conversion rate of 24DMP. In particular, the catalysts having a molar ratio of silica to alumina of 23-30 showed an extremely high conversion and no decline in 24DMP conversion with no apparent catalyst deactivation during the time on stream indicated.

Experiment 5: Effect of Pt Loading on 24DMP Cracking

In each of examples, after initial stable activity with the standard feed, a feed containing 70 wt % benzene, 15 wt % methylcyclopentane (MCP), 10 wt % 3-methylpentane (3MP), and 5 wt % of 24DMP was subjected to hydrocracking at 470° C., about WHSV 10/h and 200 psig. The feed stream contains $H_2$ ($H_2$/HC molar 4) and 50 ppm S (fed $H_2S$). The hydrocracking catalysts used were extrudates of ZSM-5 and a binder, wherein Pt was deposited on the extrudates. The silica-to-alumina molar ratio of the ZSM-5 was 50. The amount of Pt is summarized in Table 5. The result of the conversion is shown in Table 5.

TABLE 5

| | | 24DMP Conversion | | |
|---|---|---|---|---|
| Example | Catalyst Pt (wt %) | conversion (%) | averaged during tos (hr) | Deactivation rate[1] ($hr^{-1}$) |
| Ex 16 | 0.067 | 90.4 | 126-169 | $|-5.1 \times 10^{-4}|$ |
| Ex 17 | 0.079 | 93.5 | 47-71 | $|-6.0 \times 10^{-4}|$ |
| Ex 18 | 0.15 | 99.5 | 50-62 | $|-3.5 \times 10^{-4}|$ |
| Ex 19 | 0.25 | 99.8 | 59-70 | $|-1.7 \times 10^{-4}|$ |

[1]Deactivation rate: decrease of % conversion per hour calculated during time-on-stream (tos) indicated.

A higher Pt amount led to a higher conversion of 24DMP. A higher Pt amount also led to less catalyst deactivation.

Desirably, the hydrocracking catalyst, when cracking 2,4-dimethylpentane and/or 2,2,3-trimethylbutane, has a deactivation rate (i.e., decline in conversion percent) of less than the absolute value of $-3.5 \times 10^{-4}$ $hr^{-1}$ (e.g., $|-3.5 \times 10^{-4}$ $hr^{-1}|$), for example, less than or equal to $|-3.0 \times 10^{-4}$ $hr^{-1}|$, or less than or equal to $|-2.5 \times 10^{-4}$ $hr^{-1}|$, or less than or equal to $|-2.0 \times 10^{-4}$ $hr^{-1}|$, most preferably less than or equal to $|-1.0 \times 10^{-4}$ $hr^{-1}|$.

Set forth below are some embodiments of the methods disclosed herein.

Embodiment 1

A method of hydrocracking at least one of 2,4-dimethylpentane and 2,2,3-trimethylbutane, comprising: contacting a hydrocracking feed stream in the presence of hydrogen with a hydrocracking catalyst under process conditions including a temperature of 425-580° C., a pressure of 300-5000 kPa gauge and a Weight Hourly Space Velocity of 0.1-30 $h^{-1}$ to produce a hydrocracking product stream comprising benzene (e.g., comprising BTX and LPG); wherein the hydrocracking feed stream comprising $C_5$-$C_{12}$ hydrocarbons which includes at least 0.5 wt % of 2,4-dimethylpentane and/or 2,2,3-trimethylbutane, based upon a total weight of the hydrocracking feed stream; and wherein the hydrocracking catalyst comprises a hydrogenation metal in an amount of 0.010-0.30 wt % with respect to the total catalyst; and wherein the hydrocracking catalyst comprises a medium pore zeolite having a pore size of 5-6 Å and a silica to alumina molar ratio of 20-75; preferably the hydrocracking catalyst comprises a medium pore zeolite having a pore size of 5-6 Å and a silica to alumina molar ratio of 20-75 and a large pore zeolite having a pore size of 6-8 Å and a silica to alumina molar ratio of 10-80, wherein the hydrogenation metal is deposited on the medium pore zeolite and the large pore zeolite.

Embodiment 2

The process according to Embodiment 1, wherein the total amount of 2,4-dimethylpentane and 2,2,3-trimethylbutane in the hydrocracking feed stream is at least 1.0 wt %, at least 2.0 wt %, or at least 5.0 wt %, with respect to total hydrocarbon feed.

Embodiment 3

The process according to any one of Embodiments 1-2, wherein the hydrocracking catalyst comprises 0.08 to 0.25 wt % hydrogenation metal, 15 wt % to 25 wt % alumina, and a balance being the medium pore zeolite.

Embodiment 4

The process according to any one of Embodiments 1-2, wherein the hydrocracking catalyst is in the form of powder and is free from a binder.

Embodiment 5

The process according to any one of the preceding embodiments, wherein the silica to alumina molar ratio of the medium pore zeolite is in the range of 20-50, preferably 20 to 30, more preferably 21 to 29.

Embodiment 6

The process according to any one of the preceding embodiments, wherein a conversion of any 2,4-dimethylpentane is greater than or equal to 90%, preferably greater than or equal to 95%, or greater than or equal to 98%; and the conversion of any 2,2,3-trimethylbutane is greater than or equal to 90%, preferably greater than or equal to 95%, or greater than or equal to 98%.

Embodiment 7

The process according to any one of the preceding embodiments, wherein the hydrogenating metal is at least one element selected from Group 10 of the periodic table of elements, rhodium, and iridium; preferably at least one metal selected from palladium and platinum; most preferably platinum.

Embodiment 8

The process according to any one of the preceding embodiments, wherein the hydrocracking catalyst comprises at least 0.030 wt %, at least 0.050 wt %, at least 0.075 wt %, at least 0.10 wt %, at least 0.125 wt % or at least 0.20 wt %, of the hydrogenating metal in relation to the total weight of the catalyst.

Embodiment 9

The process according to any one of the preceding embodiments, wherein the hydrocracking catalyst comprises La and/or Ga, preferably at an amount of 0.10-0.40 wt % of the total weight of the catalyst.

Embodiment 10

The process according to any one of the preceding embodiments, wherein the zeolite in the hydrocracking catalyst comprises 70-100 wt % of the medium pore zeolite and 0-30 wt % of the large pore zeolite with respect to the total amount of the zeolite.

Embodiment 11

The process according to any one of the preceding embodiments, wherein the zeolite in the hydrocracking catalyst comprises 75-95 wt % of the medium pore zeolite and 5-25 wt % of the large pore zeolite with respect to the total amount of the zeolite.

Embodiment 12

The process according to any one of the preceding embodiments, wherein the process comprises separating benzene from the hydrocracking product stream.

Embodiment 13

The process according to any one of the preceding embodiments, wherein the hydrocracking catalyst has a deactivation rate of less than $|-3.5 \times 10^{-4}$ per hour$|$, preferably less than or equal to $|-3.0 \times 10^{-4}$ per hour$|$, or less than or equal to $|-2.5 \times 10^{-4}$ per hour$|$, most preferably less than or equal to $|-2.0 \times 10^{-4}$ per hour$|$.

Embodiment 14

The process according to any one of the preceding embodiments, wherein the medium pore zeolite comprises a ZSM-5.

Embodiment 15

The process according to any one of the preceding embodiments, wherein the large pore zeolite comprises a mordenite.

Embodiment 16

The process according to any one of the preceding embodiments, wherein the hydrocracking catalyst has a deactivation rate of less than or equal to $|-2.5 \times 10^{-4} \text{ hr}^{-1}|$, or less than or equal to $|-2.0 \times 10^{-4} \text{ hr}^{-1}|$, or equal to $|-1.0 \times 10^{-4} \text{ hr}^{-1}|$.

Embodiment 17

The process according to any one of the preceding embodiments, wherein a conversion percent of the 2,4-dimethylpentane and 2,2,3-trimethylbutane is greater than or equal to 95%, preferably greater than or equal to 98%, or greater than or equal to 99%, or greater than or equal to 99.5%.

Embodiment 18

The process according to any one of the preceding embodiments, wherein greater than or equal to 95%, preferably greater than or equal to 98%, more preferably, greater than or equal to 99.8%, the $C_5$-$C_{12}$ hydrocarbons are cracked.

Embodiment 19

The use of a hydrocracking catalyst to crack at least one of 2,4-dimethylpentane and 2,2,3-trimethylbutane, wherein the hydrocracking catalyst comprises a medium pore zeolite having a pore size of 5-6 Å and a silica to alumina molar ratio of 20-75; preferably the hydrocracking catalyst comprises a medium pore zeolite having a pore size of 5-6 Å and a silica to alumina molar ratio of 20-75 and a large pore zeolite having a pore size of 6-8 Å and a silica to alumina molar ratio of 10-80, wherein the hydrogenation metal is deposited on the medium pore zeolite and the large pore zeolite.

Embodiment 20

The use according to Embodiment 19, wherein the hydrocracking catalyst comprises 0.08 to 0.25 wt % hydrogenation metal, 15 wt % to 25 wt % alumina, and a balance being the medium pore zeolite.

Embodiment 21

The use according to Embodiment 19, wherein the hydrocracking catalyst is in the form of powder and is free from a binder.

Embodiment 22

The use according to any one of Embodiments 19-21, wherein the hydrogenating metal is at least one element selected from Group 10 of the periodic table of elements, rhodium, and iridium; preferably at least one metal selected from palladium and platinum; most preferably platinum.

Embodiment 23

The use according to any one of Embodiment 19-22, wherein the hydrocracking catalyst comprises at least 0.030 wt %, at least 0.050 wt %, at least 0.075 wt %, at least 0.10 wt %, at least 0.125 wt % or at least 0.20 wt %, of the hydrogenating metal in relation to the total weight of the catalyst.

Embodiment 24

The use according to any one of Embodiments 19-23, wherein the hydrocracking catalyst comprises La and/or Ga, preferably at an amount of 0.10-0.40 wt % of the total weight of the catalyst.

Embodiment 25

The use according to any one of Embodiments 19-24, wherein the zeolite in the hydrocracking catalyst comprises 70-100 wt % of the medium pore zeolite and 0-30 wt % of the large pore zeolite with respect to the total amount of the zeolite.

Embodiment 26

The use according to any one of Embodiments 19-25, wherein the zeolite in the hydrocracking catalyst comprises 75-95 wt % of the medium pore zeolite and 5-25 wt % of the large pore zeolite with respect to the total amount of the zeolite.

Embodiment 27

The use according to any one of Embodiments 19-26, wherein the hydrocracking catalyst has a deactivation rate of less than $|-3.5\times10^4$ per hour$|$, preferably less than or equal to $|-3.0\times10^4$ per hour$|$, or less than or equal to $|-2.5\times10^4$ per hour$|$, most preferably less than or equal to $|-2.0\times10^4$ per hour$|$.

Embodiment 28

The use according to any one of Embodiments 19-27, wherein the medium pore zeolite comprises a ZSM-5.

Embodiment 29

The use according to any one of Embodiments 19-28, wherein the large pore zeolite comprises a mordenite.

Embodiment 30

The use according to any one of Embodiments 19-29, wherein the silica to alumina molar ratio of the medium pore zeolite is in the range of 20-50, preferably 20 to 30, more preferably 21 to 29.

Embodiment 31

The hydrocracking catalyst accordingly to any one of Embodiments 1-30, wherein the hydrocracking catalyst can be free of metals other than the Group 10 metals of the Periodic Table of Elements, rhodium, and iridium; preferably free of metals other than palladium and platinum.

Embodiment 32

The use according to any of Embodiments 19-30 and the process according to any of Embodiments 1-18, further comprising separating the benzene from LPG, toluene and xylene, to produce a product stream, wherein the product stream has a benzene purity of greater than or equal to 99.80 wt %, preferably greater than or equal to 99.90 wt %, or greater than or equal to 99.95 wt %. It was unexpected that such a benzene purity could be obtained starting from a feed stream comprising at least 0.5 wt % of 2,4-dimethylpentane and/or 2,2,3-trimethylbutane (e.g., 0.5 wt % to 15 wt % of 2,4-dimethylpentane and/or 2,2,3-trimethylbutane), based on a total weight percent of the hydrocracking feed stream.

It is noted that the invention relates to all possible combinations of features described herein, preferred in particular are those combinations of features that are present in the claims. It will therefore be appreciated that all combinations of features relating to the composition according to the invention; all combinations of features relating to the process according to the invention and all combinations of features relating to the composition according to the invention and features relating to the process according to the invention are described herein.

It is further noted that the term 'comprising' does not exclude the presence of other elements. However, it is also to be understood that a description on a product/composition comprising certain components also discloses a product/composition consisting of these components. The product/composition consisting of these components may be advantageous in that it offers a simpler, more economical process for the preparation of the product/composition. Similarly, it is also to be understood that a description on a process comprising certain steps also discloses a process consisting of these steps. The process consisting of these steps may be advantageous in that it offers a simpler, more economical process.

As used herein, deactivation rate is the slope of conversion versus the time-on-stream (tos). If the conversion is decreasing with time on stream, the slope is negative. The absolute value of the number is relevant. The larger the absolute value the faster the catalyst is deactivating. In other words, a catalyst having a deactivation rate of $|-5.0\times10^{-4}$ hr$^{-1}|$ will deactivate 5 times faster than a catalyst having a deactivation rate of $|-1.0\times10^{-4}$ hr$^{-1}|$. Unless specified otherwise, the deactivation rate is per hour (hr$^{-1}$).

When values are mentioned for a lower limit and an upper limit for a parameter, ranges made by the combinations of the values of the lower limit and the values of the upper limit are also understood to be disclosed.

The invention claimed is:

1. A process of hydrocracking at least one of 2,4-dimethylpentane and 2,2,3-trimethylbutane, comprising:
contacting a hydrocracking feed stream comprising $C_5$-$C_{12}$ hydrocarbons in the presence of hydrogen with a hydrocracking catalyst under process conditions including a temperature of 425-580° C., a pressure of 300-5000 kPa gauge and a Weight Hourly Space Velocity of 0.1-30 to produce a hydrocracking product stream comprising LPG;
wherein the hydrocracking feed stream comprises at least 0.5 wt % of 2,4-dimethylpentane and/or 2,2,3-trimethylbutane, based upon a total weight of the hydrocracking feed stream; and
wherein the hydrocracking catalyst comprises a hydrogenation metal in an amount of 0.010-0.30 wt % with respect to the total catalyst; and
wherein the hydrocracking catalyst comprises a medium pore zeolite having a pore size of 5-6 Å and a silica to alumina molar ratio of 20-75.

2. The process according to claim 1, wherein the total amount of 2,4-dimethylpentane and 2,2,3-trimethylbutane in the hydrocracking feed stream is at least 1.0 wt %.

3. The process according to claim 1, wherein the hydrocracking catalyst comprises 0.08 to 0.25 wt % hydrogenation metal, 15 wt % to 25 wt % alumina, and a balance being the medium pore zeolite.

4. The process according to claim 1, wherein the hydrocracking catalyst is in the form of powder and is free from a binder.

5. The process according to claim 1, wherein the silica to alumina molar ratio of the medium pore zeolite is in the range of 20-50.

6. The process according to claim 5, wherein the silica to alumina molar ratio of the medium pore zeolite is in the range of 20 to 30.

7. The process according to claim 6, wherein the silica to alumina molar ratio of the medium pore zeolite is in the range of 21 to 29.

8. The process according to claim 1, wherein a conversion of any 2,4-dimethylpentane is greater than or equal to 90%; and the conversion of any 2,2,3-trimethylbutane is greater than or equal to 90%.

9. The process according to claim 1, wherein the hydrocracking catalyst comprises at least 0.030 wt %, of the hydrogenating metal in relation to the total weight of the catalyst.

10. The process according to claim 1, wherein the hydrocracking catalyst comprises La and/or Ga.

11. The process according to claim 1, wherein the process comprises separating BTX or benzene from the hydrocracking product stream.

12. The process according to claim 1, wherein greater than or equal to 95% of the $C_5$-$C_{12}$ hydrocarbons are cracked.

13. The process according to claim 1, wherein the hydrogenating metal is at least one element selected from palladium and platinum.

14. The process according to claim 1, wherein the hydrocracking feed stream comprises benzene.

15. The process according to claim 1, wherein the hydrocracking product stream comprises a greater amount of benzene compared to the hydrocracking feed stream.

16. A process of hydrocracking at least one of 2,4-dimethylpentane and 2,2,3-trimethylbutane, comprising:
contacting a hydrocracking feed stream comprising $C_5$-$C_{12}$ hydrocarbons in the presence of hydrogen with a hydrocracking catalyst under process conditions including a temperature of 425-580° C., a pressure of 300-5000 kPa gauge and a Weight Hourly Space Velocity of 0.1-30 to produce a hydrocracking product stream;
wherein the hydrocracking feed stream comprises at least 0.5 wt % of 2,4-dimethylpentane and/or 2,2,3-trimethylbutane, based upon a total weight of the hydrocracking feed stream;
wherein the hydrocracking catalyst comprises a hydrogenation metal in an amount of 0.01-0.30 wt % with respect to the total catalyst; and
wherein the hydrocracking catalyst comprises a medium pore zeolite having a pore size of 5-6 Å and a silica to alumina molar ratio of 20-75 and a large pore zeolite having a pore size of 6-8 Å and a silica to alumina molar ratio of 10-80, wherein the hydrogenation metal is deposited on the medium pore zeolite and the large pore zeolite.

17. The process according to claim 16, wherein the zeolite in the hydrocracking catalyst comprises 75-95 wt % of the medium pore zeolite and 5-25 wt % of the large pore zeolite with respect to the total amount of the zeolite.

18. The process according to claim 16, wherein the hydrocracking catalyst has a deactivation rate of less than $|-3.5\times10^{-4}$ per hour$|$.

19. The process according to claim 16, wherein the medium pore zeolite comprises a ZSM-5.

20. The process according to claim 16, wherein the large pore zeolite comprises a mordenite.

* * * * *